United States Patent [19]
Oishi

[11] Patent Number: 5,165,933
[45] Date of Patent: Nov. 24, 1992

[54] RESTRICTION ENZYME INHIBITOR

[75] Inventor: Kunio Oishi, Tokyo, Japan

[73] Assignees: Kabushikikaisha Kibun; Kabushikikaisha Kibun Fudokemifa, both of Tokyo, Japan

[21] Appl. No.: 724,449

[22] Filed: Jul. 3, 1991

Related U.S. Application Data

[62] Division of Ser. No. 382,590, Jul. 20, 1989, abandoned.

[30] Foreign Application Priority Data

Feb. 10, 1989 [JP] Japan ..................................... 1-31863

[51] Int. Cl.⁵ .............................................. A61K 35/78
[52] U.S. Cl. .................... 424/195.1; 435/183; 435/184
[58] Field of Search ..................... 424/195.1; 435/183, 435/184, 963

[56] References Cited

U.S. PATENT DOCUMENTS 4,886,756 12/1989 Kawamura et al. ................. 435/199

FOREIGN PATENT DOCUMENTS 55-18646 6/1970 Japan ..................................... 514/54
589986 1/1978 U.S.S.R. ............................... 514/54

OTHER PUBLICATIONS

"Antitumor Effects of Seaweeds. IV. Enhancement of Antitumor Activity by Sulfation of a Crude Fucoidan Fraction from Sargassum Kjellmaniamum" by Yamamoto et al. CA 101:143745m (1984).
"Separation of Sulfated Fucose-Containing Polysaccharides from Sargassum Kjellmanianum", by Nagumo et al. CA 110:54491u (1989).

*Primary Examiner*—John W. Rollins
*Attorney, Agent, or Firm*—Nixon & Vanderhye

[57] ABSTRACT

A restriction enzyme inhibitor comprising (1) a hot water extract of seaweed, (2) a precipitate from a hot water extract of seaweed in a water-miscible organic solvent, or (3) a fucoidan fraction. The restriction enzyme inhibitor can be prepared by an inexpensive and simple method and has the potential to be used for various purposes such as preventing the decomposition of DNA.

3 Claims, 2 Drawing Sheets

D: BOVIN THYMUS DNA
H: BOVIN THYMUS DNA+HindIII
1: BOVIN THYMUS DNA+HindIII+1/4 OF THE ORIGINAL SEA WEED EXTRACT
2: BOVIN THYMUS DNA+HindIII+1/16 OF THE ORIGINAL SEA WEED EXTRACT
3: BOVIN THYMUS DNA+HindIII+1/64 OF THE ORIGINAL SEA WEED EXTRACT
4: BOVIN THYMUS DNA+HindIII+1/256 OF THE ORIGINAL SEA WEED EXTRACT
5: BOVIN THYMUS DNA+HindIII+1/1024 OF THE ORIGINAL SEA WEED EXTRACT

THE FRACTION

AN AUTHENTIC SAMPLE OF FUCOSE

THE FRACTION + AN AUTHENTIC SAMPLE OF FUCOSE

RESTRICTION ENZYME INHIBITOR

This is a division of application Ser. No. 07/382,590, filed Jul. 20, 1989, now abandoned.

BACKGROUND OF THE INVENTION

The present invention relates to a restriction enzyme inhibitor comprising the hot water extract of seaweeds, etc. The restriction enzyme inhibitor of the present invention is capable of selectively inhibiting a target restriction enzyme without decomposing any exogenous DNA and it has the added advantage of ease of preparation.

Restriction enzymes are endonucleases having a site specificity for DNA which are capable of cutting and eliminating an exogenous DNA which invades cells either in the form of a virus or as naked DNA. Commonly employed restriction enzymes include HindIII, EcoRI, BamHI, BgII, PstI, etc. It is often required in practical operations of genetic engineering to prevent the decomposition of exogenous DNAs by inhibiting the action of restriction enzymes but heretofore, no restriction enzyme inhibitor has been available that can be produced by a simple method at low cost.

SUMMARY OF THE INVENTION

One object, therefore, of the present invention is to provide a restriction enzyme inhibitor that can be prepared by a simple method at low cost.

Another object of the present invention is to provide a substance that can be effectively used as an affinity ligand in the purification of restriction enzymes.

These objects can be attained by the present invention which was accomplished by the present inventors who first discovered the occurrence of restriction enzyme inhibiting activity in seaweeds.

The restriction enzyme inhibitor of the present invention is comprised of (a) a seaweed extracted with hot water, (b) a precipitate from the hot water extract of a seaweed in a water-miscible organic solvent, or (c) a fucoidan fraction.

DETAILED DESCRIPTION OF THE INVENTION

Figure 1:
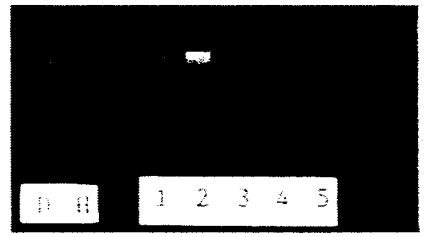
FIG. 1 shows the relationship between the sugar concentration of the hot water extract of *Pseudogloiophloea okamurai* and its ability to inhibit a restriction enzyme.

Any kind of seaweeds may be used in the present invention and illustrative examples are brown algae such as Dictyotales, Chordariales, Scytosiphonales, Laminariales and Fucales, and red algae such as Nemaliales, Gelidiales, Cryptonemiales, Gigartinales and Ceramiales. More specific examples of seaweeds that can be used in the present invention include *Ecklonia cava, Sargassum patens, Sargassum serratifolium, Undaria pinnatifida, Phyllymenia sparsa, Pseudogloiophloea okamurai, Schizymenia dubyi*, etc. These seaweeds may be used either on their own or as admixtures.

Seaweeds may be extracted by any customary method, typically by heating at 100°-120° C. for 60-70 minutes (see Example 1 to be described hereinafter). To obtain a precipitate from the extract, a water-miscible organic solvent is added and it may be selected from among any common water-miscible organic solvents including methanol, ethanol, acetone, etc. (Example 2). The fucoidan fraction which may be a component of the restriction enzyme inhibitor of the present invention may be obtained by any customary method, for example, with the aid of an additive such as a surfactant. The term "fucoidan fraction" as used herein means the residue of a seaweed from which components that do not contain fucan sulfate have been removed. A specific example of the fucoidan fraction is a fraction composed of the precipitate obtained by first extracting a seaweed with hot water and then treating it with a water-miscible organic solvent.

When seaweeds extracted with hot water were mixed with a restriction enzyme and λDNA, incubated at 37° C. for 1 hour and analyzed by electrophoresis, it was found that the activity of the restriction enzyme was inhibited significantly by the extracts (Example 3). The degree of inhibition of restriction enzymes varies with the type of seaweeds but a broad spectrum of inhibiting activity was observed whether the seaweed was a brown or red alga. In particular, seaweeds of Fucales, Nemaliales, Cryptonemiales and Gigartinales showed the necessary activity at a dose as low as 0.02 μg/ml (HindIII 12 U/μl; λDNA 0.25 μg/μl).

The hot water extracts of seaweeds prepared in accordance with the present invention proved to be effective to different extents in inhibiting various restriction enzymes (Example 4). A minimum inhibitor concentration against HindIII was in the range of 0.02-0.2 μg/ml, suggesting the appreciably high activity of the extract of the present invention. As for EcoRI and PstI, MIC was 0.2-2 μg/ml, and as for BamHI, MIC was ca. 2 μg/ml.

The present inventors undertook an investigation to know which of the components of seaweeds would be responsible for the restriction enzyme inhibiting activity exhibited by the agent of the present invention. As a result, it was found that a strong restriction enzyme inhibiting activity occurred in the fucoidan fraction (Example 4). When 0.5-4.0 parts by volume of ethanol was added to 1 part by volume of the hot water extract of seaweed, the fraction composed of a precipitate formed by adding 3.5 parts by volume of ethanol proved to have the highest activity in inhibiting restriction enzyme. The present inventors therefore hydrolyzed this fraction with HCl, acetylated the hydrolyzate and subjected the acetylated product to gas chromatographic analysis. The principal component that was detected was fucose. Since this fraction was adsorbed on an anion-exchange resin, it is suggested that the active substance should be polyfucose sulfate. These findings show that a restriction enzyme inhibiting activity occurs in the "fucoidan fraction" which contains fucan sulfate. It may therefore be safely concluded that a restriction enzyme inhibitor containing the fucoidan fraction will display useful effects irrespective of the way such fraction was obtained.

As described above, the restriction enzyme inhibitor of the present invention is capable of effectively inhibiting various restriction enzymes at low concentrations. In addition, this inhibitor can be prepared by a very simple and inexpensive method. Hence, the inhibitor has the potential for extensive use in applications where it is necessary to suppress the activity of restriction enzymes. It is also anticipated that the inhibitor may be effectively used as an affinity ligand in the purification of restriction enzymes.

The process for preparing the restriction enzyme inhibitor of the present invention and its activity are described hereinafter in greater detail.

EXAMPLE 1

Hot water extracts of seaweeds were prepared in the following way.

Various seaweeds, i.e., *Ecklonia cava, Sargassum patens, Sargassum serratifolium, Undaria pinnatifida, Phyllymenia sparsa, Pseudogloiophloea okamurai* and *Schizymenia dubyi* were washed quickly with water to remove any solid foreign matter from their surfaces. The seaweed (2 g) was thereafter shredded, mixed with water (100 ml) and heated at 120° C. for 60-70 minutes. After heating, the solids content was removed by filtration or centrifugation and the supernatant was used as the extract (concentration, 20 mg/ml; same as the concentration obtained when 20 mg of raw seaweed was extracted with 1 ml of water).

EXAMPLE 2

Precipitates from hot water extracts of seaweeds in a water-miscible organic solvents were prepared by the following method.

To 100 ml each of the extracts obtained in Example 1, 200 ml of ethanol was added and mixed. The resulting precipitate was separated by filtration or centrifugation.

EXAMPLE 3

The activity of hot water extracts of seaweeds in inhibiting a restriction enzyme was investigated by the following method.

Two milligrams, 0.2 mg or 0.02 mg of one of the selected seaweeds (i.e., brown algae including Dictyotales, Chordariales, Scytosiphonales, Laminariales and Fucales, and red algae including Nemaliales, Gilidiales, Cryptonemiales, Gigartinales and Ceramiales) was extracted with 100 ml of hot water by the method described in Example 1 to obtain extracts (the resultant concentrations were 2 μg/ml, 0.2 μg/ml and 0.02 μg/ml).

The components of a reaction solution shown in Table 1 below were charged into an Eppendorf tube in the order shown and subjected to incubation at 37° C. for 1 hour. HindIII was used as a restriction enzyme. The concentrations of λDNA and HindIII were 0.25 μg/μl and 12 U/μl, respectively.

TABLE 1

| Component | Content (μl) |
| --- | --- |
| Water | 12 |
| Buffer | 2 |

TABLE 1-continued

| Component | Content (μl) |
| --- | --- |
| Seaweed extract | 2 |
| DNA | 2 (0.5 μg) |
| Restriction enzyme solution | 2 (24 U) |
| Total | 20 |

After incubation, the reaction solution was subjected to electrophoresis through 0.6% agarose gel in the usual manner and inhibition of DNA cleavage with the restriction enzyme was examined by staining with ethidium bromide. The results are shown in Table 2.

TABLE 2

| Seaweed | Number of active species | | | |
| --- | --- | --- | --- | --- |
|  | 0.02 | 0.2 | 2[a] | Total |
| Brown algae | | | | |
| Dictyotales |  |  | 2 | 2 |
| Chordariales |  |  | 1 | 1 |
| Scytosiphonales |  |  | 3 | 3 |
| Laminariales |  | 3 | 2 | 5 |
| Fucales | 1 | 6 | 11 | 18 |
| Red algae | | | | |
| Nemaliales | 1 |  | 2 | 3 |
| Gelidiales |  |  | 2 | 2 |
| Cryptonemiales | 1 | 1 | 5 | 7 |
| Gigartinales | 2 | 2 | 8 | 12 |
| Ceramiales |  |  | 2 | 2 |

[a]Unit: μg(raw seaweed)/ml (water)
[blank spaces = not tested]

EXAMPLE 4

Inhibiting activity against various restriction enzymes was examined by the following method, with the concentration of hot water extract of seaweeds being varied.

The seaweed extracts obtained in Example 1 were serially diluted 4, 16, 64, 256 and 1024 folds and the abilities of the resulting dilutions to inhibit restriction enzyme were examined by the same method as that employed in Example 3. Profiles for *Undaria pinnatifida* are shown in FIG. 1. Maximum dilutions at which the restriction enzyme inhibiting activity was detected are shown in Table 3.

TABLE 3

| Seaweed | Threshold dilution | | | | |
| --- | --- | --- | --- | --- | --- |
|  | BamHI | BglII | EcoRI | HindIII | PstI |
| *Ecklonia cava* | 100 | <100 | 100 | 100 | 100 |
| *Sargassum patens* | 100 | <100 | 100 | 100 | <100 |
| *Sargassum serratifolium* | 100 | <100 | 100 | 1000 | 100 |
| *Undaria pinnatifida* | 100 | <100 | 100 | 100 | 100 |
| *Phyllymenia sparsa* | <100 | <100 | 1000 | 1000 | 100 |
| *Pseudogloiophloea okamurai* | 100 | <100 | 100 | 10000 | 100 |
| *Schizymenia dubyi* | 100 | <100 | 1000 | 1000 | 1000 |

EXAMPLE 5

The abilities of various fractions in seaweed to inhibit HindIII were examined by the following method.

To 1 part by volume of the hot water extract of *Ecklonia cava* obtained in Example 1, 1 part by volume of ethanol was added. The resulting precipitate was recovered by filtration and dissolved in water to make a fraction. To 1 part by volume of the supernatant, 1.5 parts by volume of ethanol was added and the resulting precipitate was recovered by filtration and dissolved in water to make another fraction. To 1 part by volume of the supernatant, 2.0 parts by volume of ethanol was added and similarly treated to obtain a third fraction. The same procedures were repeated to make other fractions, with the amount of ethanol added being increased from 2.5 through 3.0 and 3.5 to 4.0 parts by volume.

The total content of sugar in each fraction was measured by the phenol sulfate method and its activity in inhibiting restriction enzyme was examined by the same method as that employed in Example 3. The results are shown in Table 4.

TABLE 4

| Fraction (extract to ethanol ratio) | Total sugar content[a] (mg/ml) | Inhibiting activity (U) | Specific activity (U/mg/ml) |
| --- | --- | --- | --- |
| 1:0.5 | 0.53 | b | 0 |
| 1:1.5 | 0.35 | 4 | 11 |
| 1:2.0 | 0.22 | b | 0 |
| 1:2.5 | 0.68 | 10 | 15 |
| 1:3.0 | 0.31 | 10 | 32 |
| 1:3.5 | 0.92 | 40 | 43 |
| 1:4.0 | 0.30 | 10 | 33 |

[a]based on glucose
[b]not detected

Figure 2A:
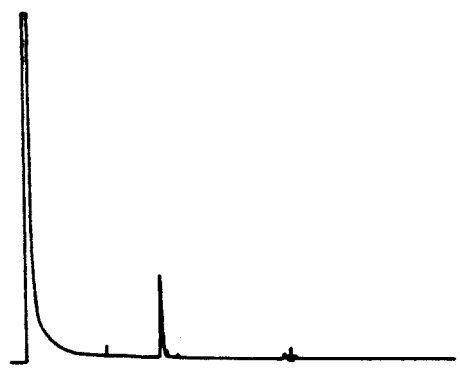
FIGS. 2(a), 2(b) and 2(c) are gas chromatograms of an extract of *Ecklonia cava*, first in a 1:3.5 extract to ethanol fraction as shown in FIG. 2(a), an authentic sample of fructose in FIG. 2(b), and a mixture of the extract fraction and the authentic sample of fructose in FIG. 2(c).
Figure 2B:
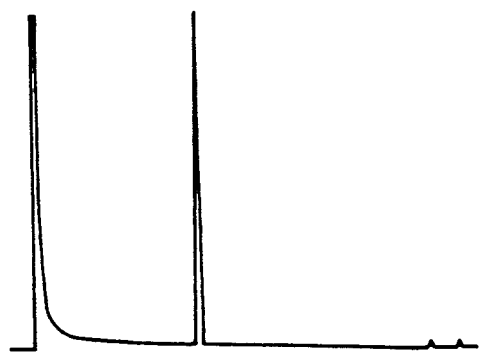
Figure 2C:

Another lot of the fraction obtained from a 1:3.5 mixture of extract and ethanol was hydrolyzed, acetylated and subjected to gas chromatographic analysis. The result is shown in FIG. 2. The sole peak that was detectable in the gas chromatogram was coincident with an authentic sample of fucose. The same fraction was loaded onto an anion-exchange resin and the resulting effluent was analyzed by gas chromatography. No peak was detected at the site corresponding to fructose. Thus as shown in FIGS. 2(a), (b) and (c), FIG. 2(a) is the gas chromatogram of that fraction of the 1:3.5 extract:ethanol referred to in Table 4 above. This shows the same single peak as is formed in the gas chromatogram of an authentic sample of fructose as in FIG. 2(b). FIG. 2(c) is a gas chromatogram of a mixture of the fraction and the authentic sample of fructose and shows a single sharp peak, indicating that the two samples are identical.

What is claimed is:

1. A method of selectively inhibiting a restriction enzyme without decomposing exogenous DNA, comprising adding to a sample containing DNA and a restriction enzyme, an enzyme-inhibiting amount of a hot water extract of Dictyotales, Chordariales, Scytosiphonales, Laminariales, Fucales, Nemaliales, Gilidiales, Cryptonemiales, Gigartinales or Ceramiales.

2. The method of claim 1 wherein a precipitate of the enzyme-inhibiting extract is added to the sample.

3. A method of selectively inhibiting a restriction enzyme without decomposing exogenous DNA, comprising adding to a sample containing DNA and a restriction enzyme, an enzyme-inhibiting amount of a fucoidan sulfate-containing fraction.

* * * * *